(12) United States Patent
Pearl, Jr. et al.

(10) Patent No.: US 11,454,113 B2
(45) Date of Patent: Sep. 27, 2022

(54) CHARACTERIZING THE BASE OIL OF A DRILLING MUD FOR COMPATIBILITY WITH SUBSEQUENT SUBTERRANEAN OPERATIONS

(71) Applicant: Halliburton Energy Services, Inc., Houston, TX (US)

(72) Inventors: William Cecil Pearl, Jr., Spring, TX (US); Megan Renee Pearl, Spring, TX (US); Samuel J. Lewis, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 486 days.

(21) Appl. No.: 16/490,810

(22) PCT Filed: Oct. 12, 2018

(86) PCT No.: PCT/US2018/055542
§ 371 (c)(1),
(2) Date: Sep. 3, 2019

(87) PCT Pub. No.: WO2020/076335
PCT Pub. Date: Apr. 16, 2020

(65) Prior Publication Data
US 2021/0108512 A1    Apr. 15, 2021

(51) Int. Cl.
*E21B 49/08*    (2006.01)
*E21B 33/14*    (2006.01)
(Continued)

(52) U.S. Cl.
CPC .............. *E21B 49/08* (2013.01); *E21B 33/14* (2013.01); *G01N 21/33* (2013.01);
(Continued)

(58) Field of Classification Search
CPC .......... C09K 8/40; C09K 8/424; C09K 8/467; C09K 8/03; C09K 8/035; C09K 8/42;
(Continued)

(56) References Cited

U.S. PATENT DOCUMENTS 3,849,316 A  * 11/1974 Motley .................. E21B 33/16
                                                          166/291
5,330,006 A     7/1994 Nahm et al.
(Continued)

FOREIGN PATENT DOCUMENTS

GB         1594184 A  *  7/1981  .............. C09K 8/40
WO     2014/093167 A1     6/2014
(Continued)

OTHER PUBLICATIONS

International Search Report and Written Opinion issued in related PCT Application No. PCT/US2018/055542 dated Jul. 10, 2019, 12 pages.

*Primary Examiner* — Zakiya W Bates
(74) *Attorney, Agent, or Firm* — Conley Rose, P.C.; Rodney B. Carroll (57) ABSTRACT

Methods and systems for determining whether a base oil for use in drilling muds will be compatible with cement during subsequent cementing operations include: providing a drilling fluid that includes a base oil; using the drilling fluid to drill at least a portion of a wellbore penetrating at least a portion of a subterranean formation; measuring a compositional characteristic of the base oil using one or more analytical tests; determining whether the base oil is a compatible base oil or an incompatible base oil based at least in part on the compositional characteristic of the base oil;

(Continued)

injecting an amount of spacer fluid into the wellbore, wherein the amount of spacer fluid is selected based on the determination of whether the base oil is a compatible base oil or an incompatible base oil; and injecting the one or more cementing or completion fluids into the wellbore.

20 Claims, 7 Drawing Sheets

(51) Int. Cl.
<table>
<tr><td>G01N 21/33</td><td>(2006.01)</td></tr>
<tr><td>G01N 21/3577</td><td>(2014.01)</td></tr>
<tr><td>G01N 24/08</td><td>(2006.01)</td></tr>
<tr><td>G01N 30/86</td><td>(2006.01)</td></tr>
<tr><td>G01N 33/28</td><td>(2006.01)</td></tr>
<tr><td>G01N 30/02</td><td>(2006.01)</td></tr>
</table>

(52) U.S. Cl.
CPC ....... *G01N 21/3577* (2013.01); *G01N 24/081* (2013.01); *G01N 30/8631* (2013.01); *G01N 33/2823* (2013.01); *G01N 2030/025* (2013.01)

(58) Field of Classification Search
CPC ....... C09K 8/502; C04B 28/02; E21B 33/138; E21B 33/13; E21B 33/14; E21B 21/003
See application file for complete search history.

(56) References Cited

U.S. PATENT DOCUMENTS

<table>
<tr><td>8,575,541 B1</td><td>11/2013</td><td>Jamison et al.</td></tr>
<tr><td>9,000,358 B2</td><td>4/2015</td><td>Jamison et al.</td></tr>
<tr><td>2004/0238170 A1</td><td>12/2004</td><td>Fanguy, Jr. et al.</td></tr>
<tr><td>2009/0188312 A1</td><td>7/2009</td><td>Sears et al.</td></tr>
<tr><td>2012/0000658 A1</td><td>1/2012</td><td>Coludrovich, III et al.</td></tr>
<tr><td>2013/0092376 A1</td><td>4/2013</td><td>Al-Subhi et al.</td></tr>
<tr><td>2014/0062489 A1*</td><td>3/2014</td><td>Pindiprolu ............ G01N 13/00 324/347</td></tr>
<tr><td>2014/0116120 A1</td><td>6/2014</td><td>Seckar</td></tr>
<tr><td>2014/0166871 A1</td><td>6/2014</td><td>Jamison et al.</td></tr>
</table>

FOREIGN PATENT DOCUMENTS

<table>
<tr><td>WO</td><td>2014/093572 A2</td><td>6/2014</td></tr>
<tr><td>WO</td><td>2015/053759 A1</td><td>4/2015</td></tr>
</table>

* cited by examiner

CHARACTERIZING THE BASE OIL OF A DRILLING MUD FOR COMPATIBILITY WITH SUBSEQUENT SUBTERRANEAN OPERATIONS

CROSS-REFERENCE TO RELATED APPLICATION

The present application is a U.S. National Stage Application of International Application No. PCT/US2018/055542 filed Oct. 12, 2018, which is incorporated herein by reference in its entirety for all purposes.

The present disclosure relates generally to well drilling, cementing and completion operations.

When an oil well is drilled, a drilling fluid (often called drilling mud) is circulated in the well. The main purposes of the drilling fluid are to lubricate the drilling operation, to control the hydrostatic pressure in the well and to convey the debris (drilling cuttings, etc.) to the surface and out of the hole. At a certain point during the drilling operation, a tubular element or casing is lowered into the drilling hole and cemented by pumping a cement slurry through the casing and into the annular space (annulus) existing between the casing and the borehole wall where it is allowed to set. This provides isolation of the formations through which the borehole passes. Cements also may be placed in other regions of a subterranean formation for many reasons, including, but not limited to, various remedial applications to strengthen those regions of a formation and prevent their collapse and to isolate a particular region of a formation from other regions therein. The strength and other properties of the cement may be tailored to the conditions in the formation, the intended function of the cement, and other factors.

During cementing and completion operations, it is possible for the cement slurry to contact residual drilling fluids or muds in the wellbore. Many drilling fluids comprise one or more base oils that may not be compatible with the cementing. In some instances, a flushing or preflushing fluid is pumped through the well before pumping the cement slurry. This flushing or preflushing fluid (which also may be referenced as a spacer fluid or spacer) has two main purposes: to drive out the drilling fluid which is initially situated in the annulus, and to separate the cement slurry and the drilling fluid since in general these two fluids are incompatible and mixing of the two can lead to problems, especially in the setting and set properties of the cement. To be capable of fulfilling these purposes, the spacer fluid used between the drilling fluid and the cement slurry should maintain stable interfaces between the different fluids and clean the walls of the borehole before the cement is placed. To obtain the good zonal isolation, the spacer fluid is used to displace as much of the drilling fluid as possible and remove residues from the surface of the casing and of the wall of the drilling hole, making it possible to obtain good bonding between the cement and the formation and between the cement and the casing.

BRIEF DESCRIPTION OF THE DRAWINGS

Some specific exemplary embodiments of the disclosure may be understood by referring, in part, to the following description and the accompanying drawings.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to well drilling, cementing and completion operations, and more particularly, to characterizing certain properties of a base oil used to drill the wellbore prior to cementing and/or other completion operations.

Illustrative embodiments of the present disclosure are described in detail herein. In the interest of clarity, not all features of an actual implementation may be described in this specification. It will of course be appreciated that in the development of any such actual embodiment, numerous implementation specific decisions are made to achieve the specific implementation goals, which will vary from one implementation to another. Moreover, it will be appreciated that such a development effort might be complex and time-consuming but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented using a tool that is made suitable for testing, retrieval and sampling along sections of the formation. Embodiments may be implemented with tools that, for example, may be conveyed through a flow passage in tubular string or using a wireline, slickline, coiled tubing, downhole robot/tractor or the like.

The present disclosure provides methods and systems for determining whether a base oil for use in drilling muds is or will be compatible with cement during subsequent cementing operations and/or other completion operations. In particular, certain base oils may negatively impact rheological properties and/or bonding strength of the cement slurry. The present disclosure provides analytical methods for determining whether a base oil may exhibit these or other undesirable impacts on cementing operations. In some embodiments, the present disclosure further provides methods for using this determination to plan for and/or minimize the potential negative impact on the cementing and completion operation.

Oil and gas hydrocarbons are naturally occurring in some subterranean formations. A subterranean formation containing oil or gas is sometimes referred to as a reservoir. A reservoir may be located under land or off shore. Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir.

A well can include, without limitation, an oil, gas, or water production well, or an injection well. As used herein, a "well" includes at least one wellbore. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region of the formation. The near-wellbore region is generally considered to be the region of the formation within about 100 feet of the wellbore. As used herein, "into a well" means and includes into any portion of the well, including into the wellbore or into the near-wellbore region of the formation via the wellbore.

A portion of a wellbore may be an open hole or cased hole. In an open-hole portion of a wellbore, a tubing string may be placed into the wellbore. The tubing string allows fluids to be introduced into or flowed from a remote portion of the wellbore. In a cased-hole portion of a wellbore, a casing is placed into the wellbore, which can also contain a tubing string. A wellbore can contain an annulus. Examples of an annulus include, but are not limited to: the space between the wellbore and the outside of a tubing string in an open-hole wellbore; the space between the wellbore and the outside of a casing in a cased-hole wellbore; and the space between the inside of a casing and the outside of a tubing string in a cased-hole wellbore.

During well operations, it is common to introduce drilling fluids, sometimes referred to as drilling muds, into the wellbore. These drilling muds can be selected from water-based muds (including oil-in-water emulsions), oil-based muds (including water-in-oil emulsions) and gaseous muds. In some embodiments, drilling muds may include clays, heavy-weight additives and viscosifiers suspended in either a water or oil-based fluid. In some embodiments, the clays may comprise a combination of native clays and bentonite, a three-layer clay that swells in the presence of water. When the drilling muds are being pumped into the wellbore, they may be in a thin, free-flowing liquid phase. However, when the pumping is stopped, the static fluids form a gel that resists flow. In many instances, it may be difficult to remove the drilling mud from the wellbore when it is in its gel form versus its liquid form.

During well completion, it is also common to introduce a cement composition into an annulus in a wellbore using a process often referred to as well cementing. Cement compositions can also be used in primary or secondary cementing operations, well-plugging, squeeze cementing, or gravel packing operations.

Generally, the borehole into which the casing or liner to be cemented is installed is filled with drilling fluid. However, this may create several problems. Conventional cement and drilling fluids may be incompatible with each other. Thus, as the cement is forced down the casing or liner and up into the annulus it may be mixed with the drilling fluid at any interface between the mud and the cement. The resulting mixture generally thickens or becomes a gel and does not set up into a strong cement. In addition, the gel strength and viscosity become uncontrollable and the mixture may either become too viscous to pump or may get thinner. If the mixture gets thinner, it can allow solids to settle downward in the annulus where they may bridge and restrict the passage of the cement slurry.

The presence of gelled drilling mud in the annulus may impair the rheological and mechanical properties of the cement composition, such as compressive strength development and the ability of the cement composition to set properly in the wellbore. Such situations can lead to poor bonding between the cement composition and the formation, as well as between the cement composition and the casing. In some instances, a spacer fluid may be circulated in the wellbore to remove the drilling mud before cementing operations. The spacer fluid may comprise one or more surfactants that may aid in removal of the drilling mud. However, such spacer fluids may not entirely remove the drilling mud, especially any gelled drilling mud. Therefore, a drilling mud that could remain in fluid form in the wellbore and mix with cement compositions without impairing the rheological, cementitious, and mechanical properties of a cementing operation would be advantageous. A base oil may be selected specifically for its ability to mix with subsequent cement compositions without negative impact. A wide variety of base oils are commercially available for use in manufacturing drilling muds. Examples of such base oils are commonly sold under one or more trade names, such as ACCOLADE®, ENCORE®, INTERGRADE®, and INNOVERT®, which are commercially available from Halliburton Energy Services, Inc., Houston, Tex.

Before, or instead of, cementing operations, various completion operations may be performed to enhance or restore the productivity of oil and gas from a well. Stimulation treatments fall into two main groups: hydraulic fracturing and matrix treatments. Fracturing treatments are performed above the fracture pressure of the subterranean formation to create or extend a highly permeable flow path between the formation and the wellbore. Matrix treatments are performed below the fracture pressure of the formation. Other types of completion operations can include, for example, gravel packing, consolidation, and controlling excessive water production.

The present disclosure provides numerous analytical methods to determine whether a particular batch of base oil is a "compatible" base oil or an "incompatible" base oil with regard to its ability to interact favorably with fluids used in subsequent cementing and/or completion operations. Differences in the compositional characteristics of the base oil used to form a particular drilling fluid may negatively impact subsequent cementing or completion operations. A base oil with one compositional characteristics profile may be a compatible base oil for certain subsequent cementing and/or completion operations while a base oil with a second compositional characteristics profile may be an incompatible base oil for those same subsequent cementing and/or completion operations. Alternatively, a base oil with a compositional characteristics profile may be a compatible base oil for certain subsequent cementing and/or completion operations while it is an incompatible base oil for other subsequent cementing and/or completion operations. As used herein, the term "compatible base oil" refers to a base oil (e.g., a particular batch or lot of a base oil) that is expected to be capable of mixing with cement compositions and completion fluids to be used subsequently in the well (e.g., cement compositions and/or completion fluids with which the base oil is expected to come into contact) without impairing their rheological, cementitious, and/or mechanical properties and that meets these expectations during subsequent cementing and/or completion operations. For example, a compatible base oil may be able to mix with a subsequently-used cementing or completion fluid without negatively impacting said cementing or completion operations. As used herein, the term "incompatible base oil" refers to a base oil (e.g., a particular batch or lot of a base oil) that, when mixed with cement compositions and completion fluids to be used subsequently in the well (e.g., cement compositions and/or completion fluids with which the base oil is expected to come into contact), would be expected to impair their rheological, cementitious, and/or mechanical properties, and that does not meet these expectations during subsequent cementing and/or completion operations. For example, an incompatible base oil may not be able to mix with a subsequent cementing or completion fluid without negatively impacting said cementing or completion operations. However, an incompatible base oil may not render subsequent cementing or completion operations completely ineffective. Instead, the incompatible base oil may cause the cementing or completion operations to have less desirable results than would be experienced if a compatible base oil had been used.

In some embodiments, variations of compositional characteristics may occur within batches of commercially available base oil that is marketed under the same trade name or as meeting the same standards such that some batches would be deemed a compatible base oil and other batches would be deemed an incompatible base oil. Because the variation between batches often consists of only minor compositional differences, the nominal, reported chemical makeup provided by the manufacturer and overall effectiveness of the base oil during drilling operations may not be impacted despite these differences. For example, in certain embodiments, slight variations in the compositional characteristics, such as chemical makeup of the drilling mud, may negatively impact its ability to mix with cement without causing harm during drilling operations. In some embodiments, these compositional characteristics may include the degree of isomerization of the base oil. In other embodiments, these compositional characteristics may include the ratio of carbon chain lengths found in the base oil.

Without intending to be limited to any particular mechanism, it is believed that minor differences in the isomerization of a particular batch or lot of the base oil may result in a drilling fluid that is not compatible with subsequent cementing and/or completion operations, even though a previous batch of that same base oil may have been compatible with those operations. For example, many base oils may comprise one or more long-chain hydrocarbons. These hydrocarbon chains may be saturated or unsaturated and may contain one or more branched chains. Depending on the degree of saturation and the location of any branched chains, different isomers sharing the same overall chemical formula may occur. Accordingly, a manufacturer or vendor may market or sell two batches of a base oil that have the same nominal chemical formula but may have significantly different carbon composition profiles. For example, the chemical formula $C_5H_{12}$ may exist in several different isomers, such as pentane:

2-methyl butane:

and
2,2-dimethylpropane:

Although these three compounds share a common chemical formula, each may exhibit different chemical or physical properties.

The compositional characteristics, including isomerization, of different base oils and/or different batches or lots of a single type of base oil may be measured using one or more analytical tests. For example, in some embodiments, a suitable analytical test may be one that is capable of determining the degree of branching or saturation of a chemical structure. In certain embodiments, the compositional characteristics may be measured using any suitable analytical test(s) for determining the compositional characteristics of a compound, including but not limited to nuclear magnetic resonance ("NMR") spectroscopy, ion chromatography, gas chromatography, ultraviolet-visible ("UV-Vis") spectroscopy, infrared spectroscopy, or any combination or variant thereof. In some embodiments, one or more of these tests may be performed at an off-site location such as a warehouse, off-site laboratory, or center of operations. The results of said testing then may be carried or otherwise communicated (e.g., along with the base oil itself) to the well site for use by the operators. In other embodiments, one or more of the analytical tests described above may be performed at a laboratory located at the well-site before, during, or after drilling operations.

As discussed above, in some embodiments, the analytical test(s) may include NMR spectroscopy. NMR spectroscopy is a spectroscopic technique used to observe local magnetic fields around atomic nuclei. A sample of unknown structure may be placed in a magnetic field and the NMR signal may be produced by excitation of the nuclei sample with radio waves into nuclear magnetic resonance, which is detected with sensitive radio receivers. The intramolecular magnetic field around an atom in a molecule changes the resonance frequency, thereby providing details of the electronic structure of a molecule and its individual chains or functional groups. Therefore, in some embodiments, the peaks presented by two different NMR spectra may be compared to determine slight differences in compositional characteristics, including isomerization, of a compound.

In other embodiments, the analytical test(s) may include ion chromatography. Ion chromatography is a chromatography process that separates ions and polar molecules based on their affinity to an ion exchanger. In other words, ion chromatography separates molecules based on their respective charged groups. The ion chromatography process may be used to generate an ion chromatogram showing peaks that are representative of the charged groups found in an unknown structure or mixture. Therefore, in some embodiments, the peaks presented by two different ion chromatograms may be compared to determine slight differences in compositional characteristics, including isomerization, of a compound.

In still other embodiments, the analytical test(s) may include gas chromatography. Gas chromatography is a chromatography process used in analytical chemistry for separating and analyzing compounds that can be vaporized without decomposition. A gas chromatograph uses a flow-through narrow tube known as the column, through which different chemical constituents of a sample pass in a gas stream at different rates depending on their various chemical and physical properties and their interaction with a specific column filling. Alternatively, gas chromatography may be used to separate chemicals based on their charge to mass ration in a time of flight method. As the chemicals exit the end of the column, they are detected and identified electronically and recorded as peaks on a chromatogram. Therefore, in some embodiments, the peaks presented by two different gas chromatograms may be compared to determine slight differences in compositional characteristics, including isomerization, of a compound.

In still other embodiments, the analytical test(s) may include UV-Vis spectroscopy. UV-Vis spectroscopy is a spectroscopy process used in analytical chemistry for the quantitative determination of different analytes based on their absorption or reflectance of light in the visible range. Molecules containing n-electrons or non-bonding electrons (n-electrons) can absorb energy in the form of ultraviolet or visible light to excite these electrons to higher anti-bonding molecular orbitals. The more easily excited the electrons, the longer the wavelength of light it can absorb. Therefore, in some embodiments, the spectra from two different unknown samples may be compared to determine slight differences in compositional characteristics, including isomerization, of a compound.

In still other embodiments, the analytical test(s) may include infrared spectroscopy. Infrared spectroscopy is a spectroscopy process used in analytical chemistry for the quantitative determination of different analytes based on the interaction of infrared radiation with matter. Infrared spectroscopy relies on a molecule's abilities to absorb radiation frequencies that are characteristic of their structure. These absorptions occur at resonant frequencies, i.e., the frequency of the absorbed radiation matches the vibrational frequency. Therefore, in some embodiments, the peaks presented by two different infrared spectra may be compared to determine slight differences in compositional characteristics, including isomerization, of a compound.

In some embodiments, the results of one or more of the above analytical tests described below for a candidate base oil may be compared with the results received from a known compatible base oil (e.g., a base oil known to be compatible with the subsequent cementing and/or completion operations). If the results are identical, then the new oil will likely perform well when the cement comes into contact with the drilling mud in the well and may be classified as a compatible base oil. If the results are substantially different, then the oil may perform poorly when the cement comes into contact with the drilling mud in the well and may be classified as an incompatible base oil.

In some embodiments, following a determination that the drilling mud contains a base oil classified as an incompatible base oil having undesirable characteristics, it may be possible to adjust operational parameters of the cleaning steps to account for and/or minimize the negative consequences of using that incompatible base oil. For example, in certain embodiments, it may be possible to minimize the impact of a drilling mud that comprises an incompatible base oil by increasing the quantity of spacer fluid that is circulated through the well prior to cementing and/or completion operations. As explained above, the spacer fluid may be injected into the well to remove the drilling mud from the well before cementing and/or completion operations. Accordingly, if the drilling mud comprises an incompatible base oil it may be advantageous to inject a greater amount, or volume, of spacer fluid, such as by increasing the flow rate of the spacer fluid into the well or by injecting the spacer fluid into the well for a longer period of time. The increased amount, or volume, of the spacer fluid may result in greater removal of the incompatible base oil from the well. In other embodiments, it may also be possible to add a greater amount of surfactants to the spacer fluid before it is injected into the wellbore. For example, it may be possible to increase the overall concentration of the surfactants in the treatment fluid. The increased concentration may improve the ability of the spacer fluid to remove the incompatible base oil from the wellbore. In still other embodiments, it may be possible to select different types of surfactants to aid in the removal of the drilling mud that comprises an incompatible base oil. For example, over time an operator may be able to associate the results received from the one or more analytical tests above with a known incompatible base oil. Based at least in part on prior experience with the known incompatible base oil, the operator may know that certain surfactants are more or less effective at removing the incompatible base oil from the wellbore. Accordingly, the operator may be able to select a more effective surfactant for use with a particular incompatible base oil. In other embodiments, the operator may be able to add surfactants directly to the cement or completion fluid to compensate for the effects of the incompatible base oil. However, such spacer fluids and surfactants may be expensive and may require extensive amount of time to remove the drilling mud. Thus, it may not be feasible to use large quantities of the spacer fluids and surfactants in some instances.

Figure 1:
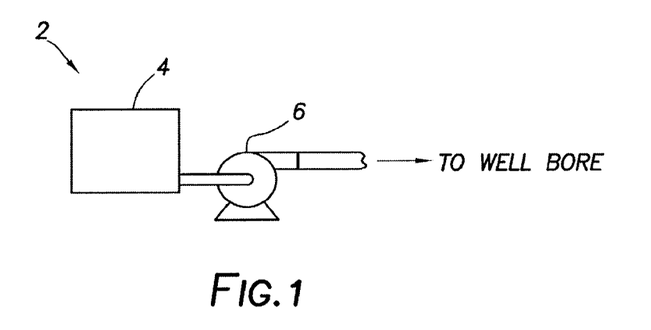
FIG. 1 is a schematic representation of a system that may be used in the preparation of a cement composition in accordance with certain embodiments.

Referring now to FIG. 1, a system that may be used in the preparation of a cement composition in accordance with example embodiments will now be described. FIG. 1 illustrates a system 2 for preparation of a cement composition and delivery to a well bore in accordance with certain embodiments. As shown, the cement composition may be mixed in mixing equipment 4, such as a jet mixer, re-circulating mixer, or a batch mixer, for example, and then pumped via pumping equipment 6 to the well bore. In some embodiments, the mixing equipment 4 and the pumping equipment 6 may be disposed on one or more cement trucks as will be apparent to those of ordinary skill in the art. In some embodiments, a jet mixer may be used, for example, to continuously mix the composition, including water, as it is being pumped to the well bore.

Figure 2A:
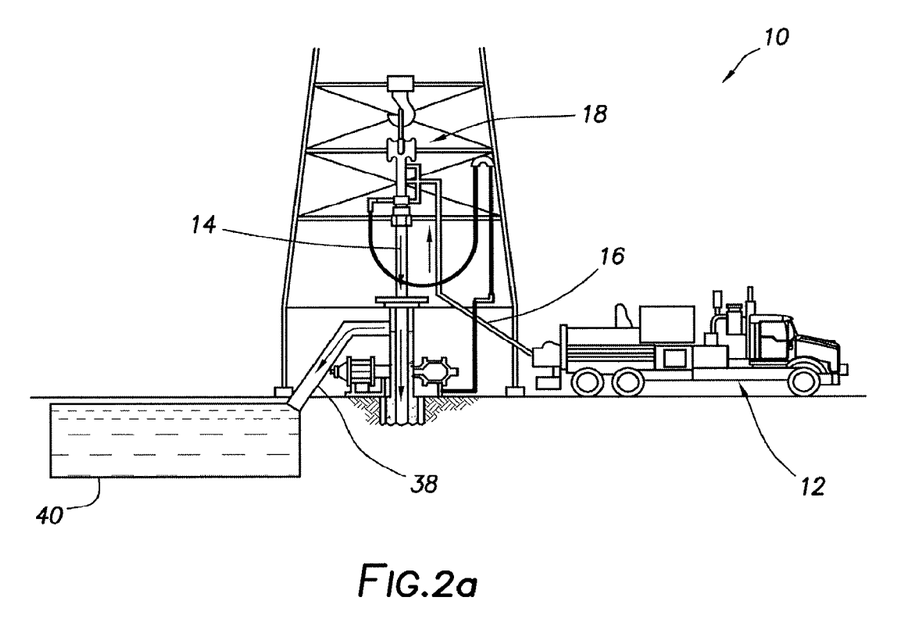
FIG. 2a is a schematic representation of surface equipment that may be used in placement of a cement composition in accordance with certain embodiments.

An example technique and system for placing a cement composition into a subterranean formation will now be described with reference to FIGS. 2a and 2b. FIG. 2a illustrates surface equipment 10 that may be used in placement of a cement composition in accordance with certain embodiments. It should be noted that while FIG. 2a generally depicts a land-based operation, those skilled in the art will readily recognize that the principles described herein are equally applicable to subsea operations that employ floating or sea-based platforms and rigs, without departing from the scope of the disclosure. As illustrated by FIG. 2a, the surface equipment 10 may include a cementing unit 12, which may include one or more cement trucks. The cementing unit 12 may include mixing equipment 4 and pumping equipment 6 (e.g., FIG. 1) as will be apparent to those of ordinary skill in the art. The cementing unit 12 may pump a cement composition 14 through a feed pipe 16 and to a cementing head 18 which conveys the cement composition 14 downhole.

Figure 2B:
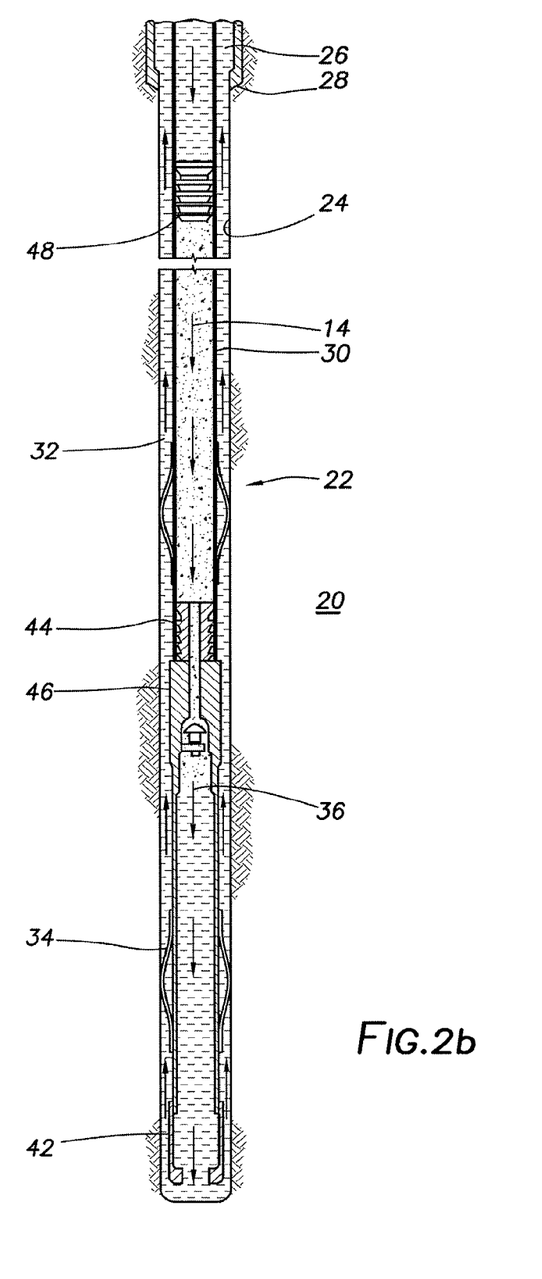
FIG. 2b is a schematic representation of downhole equipment that may be used in placement of a cement composition in accordance with certain embodiments.

Turning now to FIG. 2b, the cement composition 14 may be placed into a subterranean formation 20 in accordance with example embodiments. As illustrated, a well bore 22 may be drilled into the subterranean formation 20. While well bore 22 is shown extending generally vertically into the subterranean formation 20, the principles described herein are also applicable to well bores that extend at an angle through the subterranean formation 20, such as horizontal and slanted well bores. As illustrated, the well bore 22 comprises walls 24. In the illustrated embodiments, a surface casing 26 has been inserted into the well bore 22. The surface casing 26 may be cemented to the walls 24 of the well bore 22 by cement sheath 28. In the illustrated embodiment, one or more additional conduits (e.g., intermediate casing, production casing, liners, etc.) shown here as casing 30 may also be disposed in the well bore 22. As illustrated, there is a well bore annulus 32 formed between the casing 30 and the walls 24 of the well bore 22 and/or the surface casing 26. One or more centralizers 34 may be attached to the casing 30, for example, to centralize the casing 30 in the well bore 22 prior to and during the cementing operation.

With continued reference to FIG. 2b, the cement composition 14 may be pumped down the interior of the casing 30. The cement composition 14 may be allowed to flow down the interior of the casing 30 through the casing shoe 42 at the bottom of the casing 30 and up around the casing 30 into the well bore annulus 32. The cement composition 14 may be allowed to set in the well bore annulus 32, for example, to form a cement sheath that supports and positions the casing 30 in the well bore 22. While not illustrated, other techniques may also be utilized for introduction of the cement composition 14. By way of example, reverse circulation techniques may be used that include introducing the cement composition 14 into the subterranean formation 20 by way of the well bore annulus 32 instead of through the casing 30.

As it is introduced, the cement composition 14 may displace other fluids 36, such as drilling fluids and/or spacer fluids, that may be present in the interior of the casing 30 and/or the well bore annulus 32. At least a portion of the displaced fluids 36 may exit the well bore annulus 32 via a flow line 38 and be deposited, for example, in one or more retention pits 40 (e.g., a mud pit), as shown on FIG. 2a. Referring again to FIG. 2b, a bottom plug 44 may be introduced into the well bore 22 ahead of the cement composition 14, for example, to separate the cement composition 14 from the fluids 36 that may be inside the casing 30 prior to cementing. After the bottom plug 44 reaches the landing collar 46, a diaphragm or other suitable device ruptures to allow the cement composition 14 through the bottom plug 44. In FIG. 2b, the bottom plug 44 is shown on the landing collar 46. In the illustrated embodiment, a top plug 48 may be introduced into the well bore 22 behind the cement composition 14. The top plug 48 may separate the cement composition 14 from a displacement fluid 50 and also push the cement composition 14 through the bottom plug 44.

To facilitate a better understanding of the present disclosure, the following examples of certain aspects of certain embodiments are given. The following examples are not the only examples that could be given according to the present disclosure and are not intended to limit the scope of the disclosure or claims.

Example

In this example, two illustrative base oils composed of unsaturated hydrocarbons are compared. Both samples were prepared from different batches of the same nominal base oil supplied by the same vendor. The carbon distribution showing the percentages of various carbon chain lengths detected in the two base oils is shown in Table 1.

TABLE 1

Carbon distribution of base oil samples

|  | Sample 1 | Sample 2 |
| --- | --- | --- |
| ≤C14 | 0.56% | 0.18% |
| C15 | 13.30% | 1.47% |
| C16 | 43.92% | 58.18% |
| C17 | 13.88% | 2.06% |
| C18 | 24.39% | 33.92% |
| ≥C19 | 3.94% | 4.20% |

As can be seen in Table 1, Sample 1 contains significant quantities of C15 and C17 in addition to C16 and C18 whereas Sample 2 contains almost exclusively C16 and C18. While some operators might consider Sample 1 and Sample 2 functionally interchangeable, the differences between the two samples could have significant impacts on subsequent cementing and/or completions operations. For example, the base oil identified as Sample 2 may perform well when it comes into contact with cement, while the base oil identified as Sample 1 may perform poorly when it comes into contact with cement.

Figure 3A:
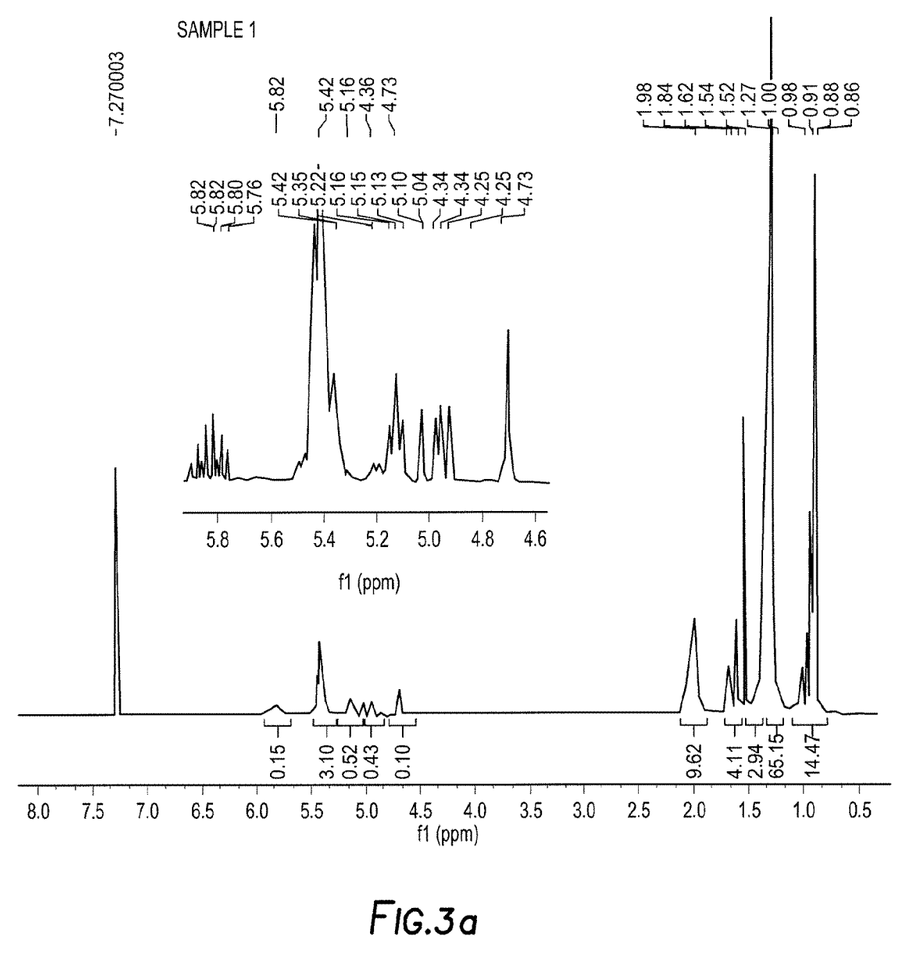
FIG. 3a is a diagram showing NMR spectrograms of oil samples in accordance with certain embodiments.
Figure 3B:
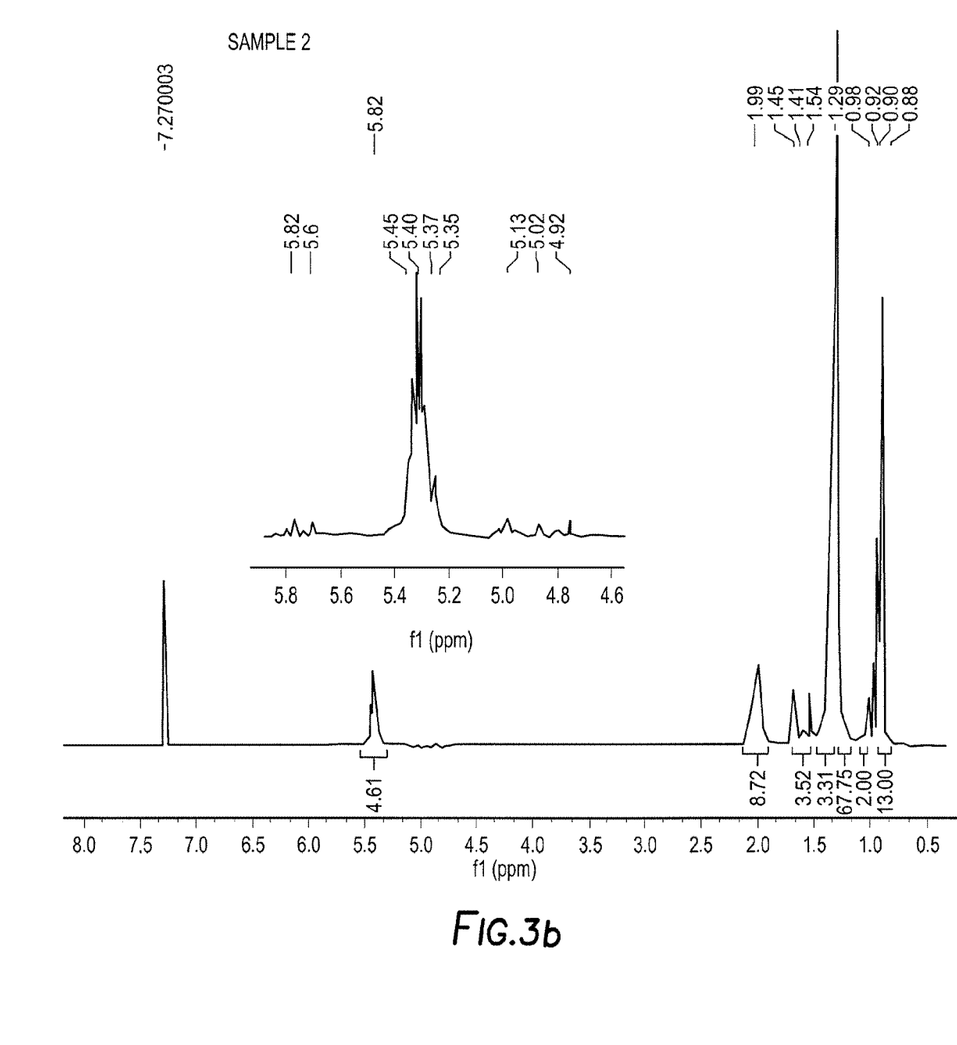
FIG. 3b is a diagram showing NMR spectrograms of oil samples in accordance with certain embodiments.
Figure 4A:
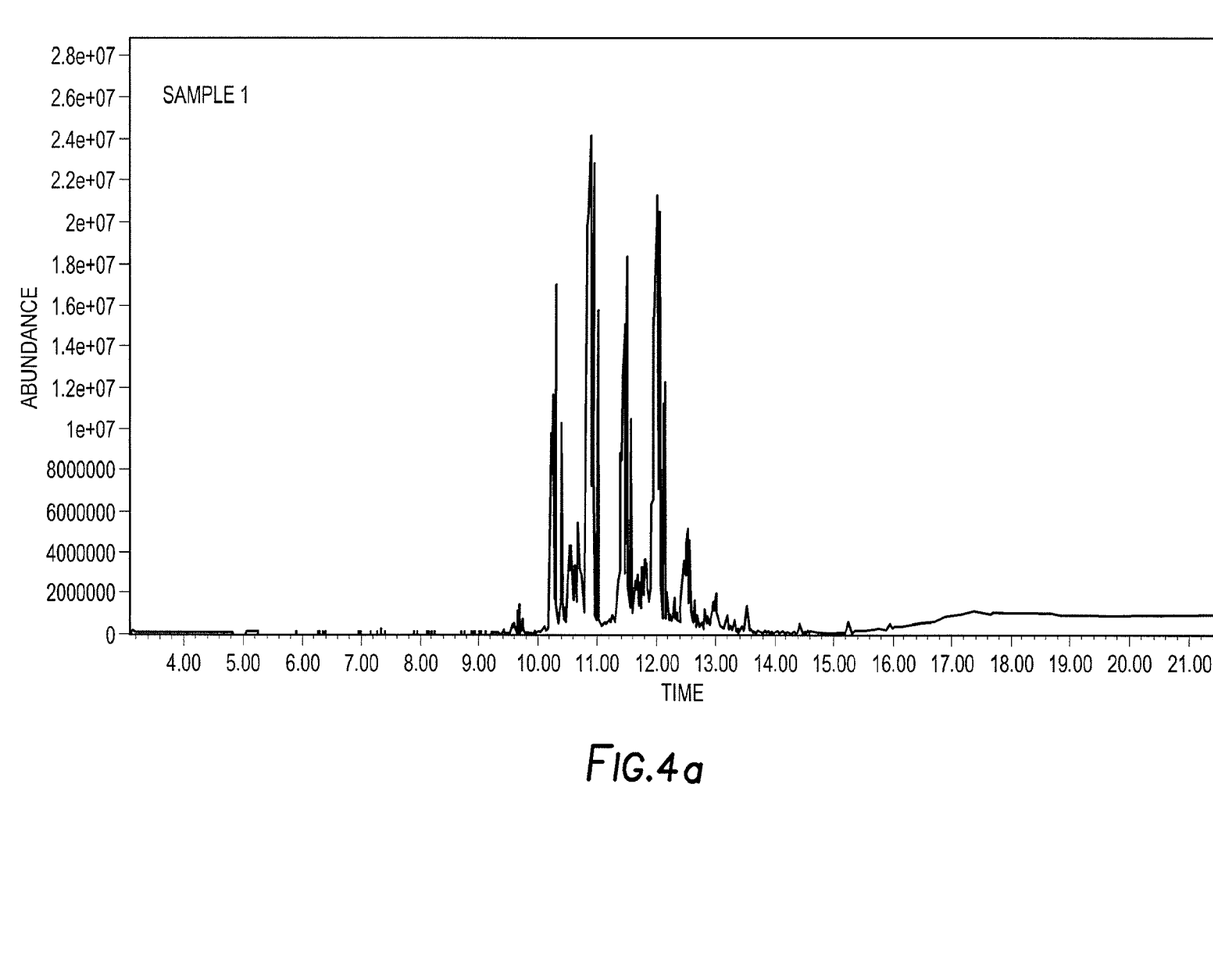
FIG. 4a is a diagram showing ion chromatograms of oil samples in accordance with certain embodiments.
Figure 4B:
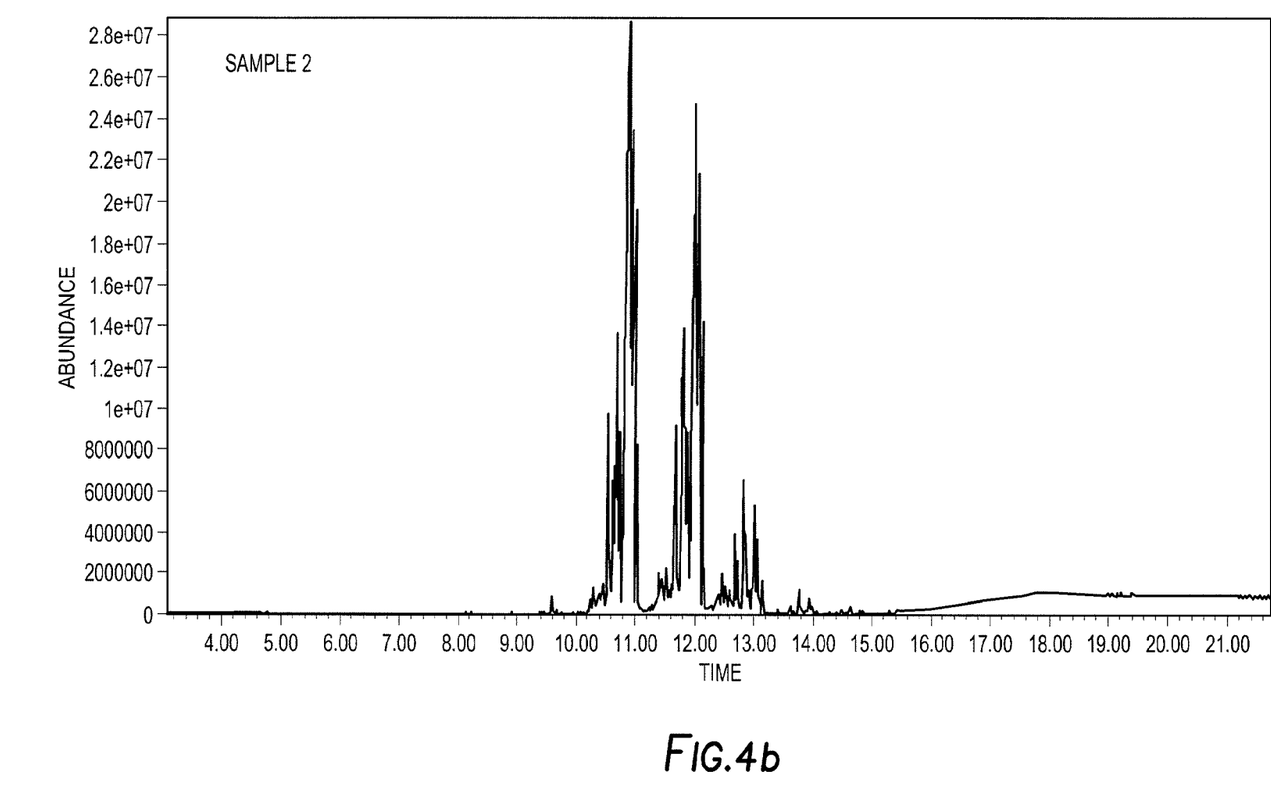
FIG. 4b is a diagram showing ion chromatograms of oil samples in accordance with certain embodiments.
Figure 5:
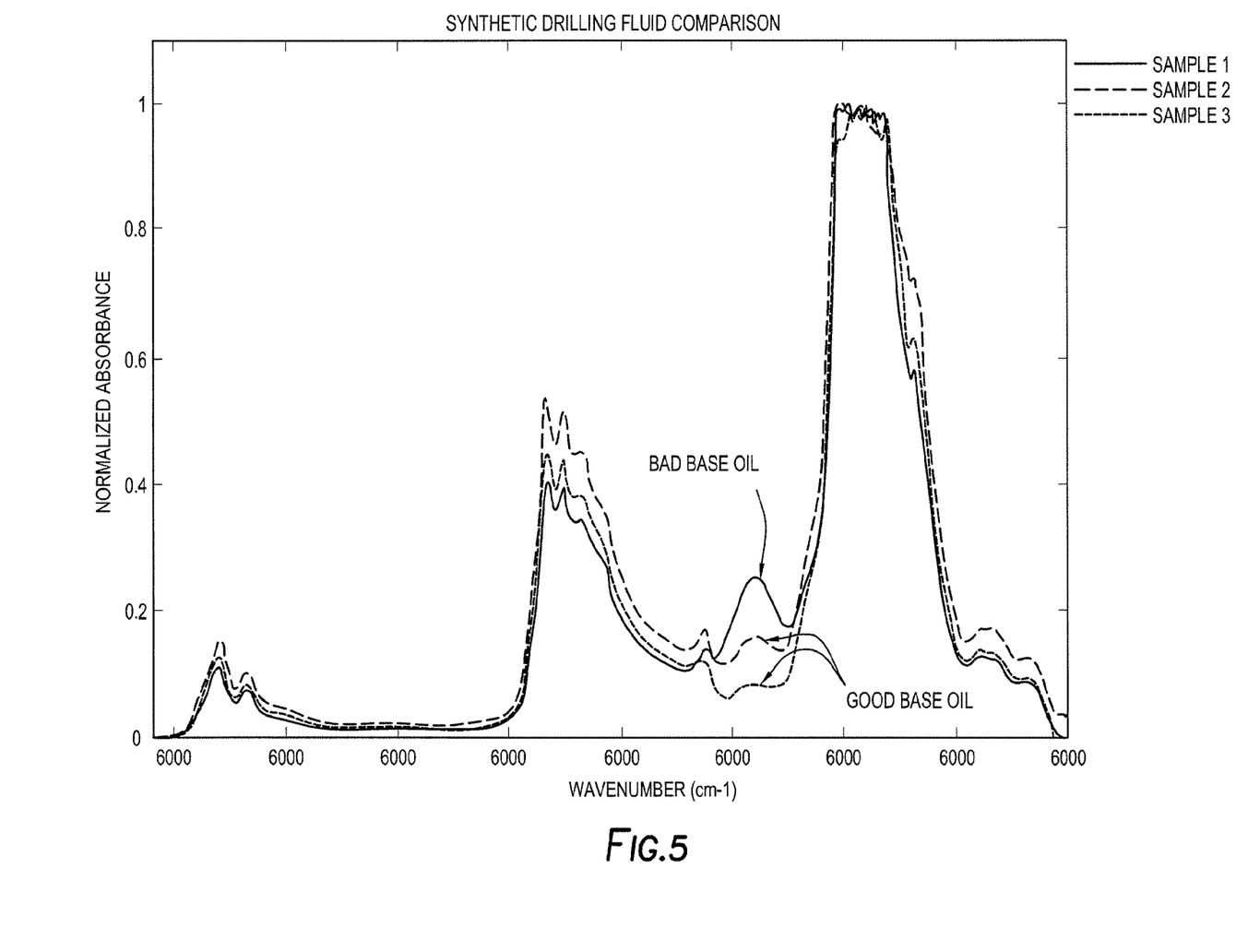
FIG. 5 is a diagram showing infrared spectrograms of oil samples in accordance with certain embodiments.

As discussed above, the composition of Sample 1 and Sample 2 may be measured using various analytical methods. For example, FIG. 3a shows an NMR spectrogram of Sample 1. FIG. 3b shows an NMR spectrogram of Sample 2. Sample 1 and 2 have the same prominent peaks but sample 1 has additional peaks in the range of 4.7 to 5.9 ppm from the undesired contaminant. Further, FIG. 4a shows an ion chromatogram of Sample 1. FIG. 4b shows an ion chromatogram of Sample 2. The ion chromatogram for sample 1 shows significantly higher portions of C15 and C17 than that of sample 2. Finally, FIG. 5 shows a comparison of infrared spectrograms of Sample 1 and Sample 2. The infrared spectrographs show there is a clear difference in the ratio of peak heights that can be used to differentiate the two samples of oil by this method of analysis.

An embodiment of the present disclosure is a method that includes: providing a drilling fluid that includes a base oil; using the drilling fluid to drill at least a portion of a wellbore penetrating at least a portion of a subterranean formation; measuring a compositional characteristic of the base oil using one or more analytical tests; determining whether the base oil is a compatible base oil or an incompatible base oil based at least in part on the compositional characteristic of the base oil; injecting an amount of spacer fluid into the wellbore, wherein the amount of spacer fluid is selected based on the determination of whether the base oil is a compatible base oil or an incompatible base oil; and injecting one or more cementing or completion fluids into the wellbore.

In one or more embodiments described in the preceding paragraph, the one or more analytical tests include a nuclear magnetic resonance spectroscopy test. In one or more embodiments described above, the one or more analytical tests include an infrared spectroscopy test. In one or more embodiments described above, the one or more analytical tests include a gas chromatography test. In one or more embodiments described above, the one or more analytical tests include an ion chromatography test. In one or more embodiments described above, the one or more analytical tests include an ultraviolet-visible spectroscopy test. In one or more embodiments described above, the step of determining whether the base oil is a compatible base oil or an incompatible base oil further includes comparing the compositional characteristics of the base oil with one or more known compositional characteristics of a known compatible base oil. In one or more embodiments described above, the step of injecting an amount of spacer fluid into the wellbore further includes increasing the amount of spacer fluid if the base oil is an incompatible base oil. In one or more embodiments described above, the step of injecting an amount of spacer fluid into the wellbore further includes adding an amount of a surfactant to the spacer fluid if the base oil is an incompatible base oil. In one or more embodiments described above, the step of measuring a compositional characteristic of the base oil using one or more analytical tests occurs at a location proximate to the wellbore. In one or more embodiments described above, the step of measuring a compositional characteristic of the base oil using one or more analytical tests occurs at a location apart from the wellbore.

Another embodiment of the present disclosure is a method that includes: providing a drilling fluid that includes a base oil; using the drilling fluid to drill at least a portion of a wellbore penetrating at least a portion of a subterranean formation; measuring a compositional characteristic of the base oil using one or more analytical tests; determining whether the base oil is a compatible base oil or an incompatible base oil based at least in part on a comparison of the compositional characteristic of the base oil with one or more known compositional characteristics of a known compatible base oil; injecting an amount of spacer fluid that comprises an amount of a surfactant into the wellbore, wherein the amount of the surfactant is increased if the base oil is an incompatible base oil; and injecting one or more cementing or completion fluids into the wellbore.

In one or more embodiments described in the preceding paragraph, the one or more analytical tests include a nuclear magnetic resonance spectroscopy test. In one or more embodiments described above, the one or more analytical tests include an infrared spectroscopy test. In one or more embodiments described above, the one or more analytical tests include a gas chromatography test. In one or more embodiments described above, the one or more analytical tests include an ion chromatography test. In one or more embodiments described above, the one or more analytical tests include an ultraviolet-visible spectroscopy test. In one or more embodiments described above, the step of injecting an amount of spacer fluid into the wellbore further includes increasing the amount of the spacer fluid if the base oil is an incompatible base oil.

Another embodiment of the present disclosure is a method that includes: providing a drilling fluid that includes a base oil; using the drilling fluid to drill at least a portion of a wellbore penetrating at least a portion of a subterranean formation; measuring a compositional characteristic of the base oil using one or more analytical tests; determining whether the base oil is a compatible base oil or an incompatible base oil based at least in part on a comparison of the compositional characteristic of the base oil with one or more known compositional characteristics of a known compatible base oil; providing one or more cementing or completion fluids, wherein the one or more cementing or completion fluids comprise a surfactant if the base oil is an incompatible base oil; and injecting the one or more cementing or completion fluids into the wellbore.

In one or more embodiments described in the preceding paragraph, the one or more analytical tests are selected from the group consisting of a nuclear magnetic resonance spectroscopy test, an infrared spectroscopy test, a gas chromatography test, an ion chromatography test, an ultraviolet-visible spectroscopy test, and any combinations thereof.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The indefinite articles "a" or "an," as used in the claims, are defined herein to mean one or more than one of the element that it introduces. Also, the terms in the claims have their plain, ordinary meaning unless otherwise explicitly and clearly defined by the patentee.

What is claimed is:

1. A method comprising:
   providing a drilling fluid that comprises a base oil;
   using the drilling fluid to drill at least a portion of a wellbore penetrating at least a portion of a subterranean formation;
   measuring a compositional characteristic of the base oil using one or more analytical tests;
   determining whether the base oil is a compatible base oil or an incompatible base oil based at least in part on the compositional characteristic of the base oil;
   injecting an amount of spacer fluid into the wellbore, wherein the amount of spacer fluid is selected based on the determination of whether the base oil is a compatible base oil or an incompatible base oil; and
   injecting one or more cementing or completion fluids into the wellbore.

2. The method of claim 1, wherein the one or more analytical tests comprises a nuclear magnetic resonance spectroscopy test.

3. The method of claim 1, wherein the one or more analytical tests comprises an infrared spectroscopy test.

4. The method of claim 1, wherein the one or more analytical tests comprises a gas chromatography test.

5. The method of claim 1, wherein the one or more analytical tests comprises an ion chromatography test.

6. The method of claim 1, wherein the one or more analytical tests comprises an ultraviolet-visible spectroscopy test.

7. The method of claim 1, wherein the step of determining whether the base oil is a compatible base oil or an incompatible base oil further comprises comparing the compositional characteristics of the base oil with one or more known compositional characteristics of a known compatible base oil.

8. The method of claim 1, wherein the step of injecting an amount of spacer fluid into the wellbore further comprises increasing the amount of spacer fluid if the base oil is an incompatible base oil.

9. The method of claim 1, wherein the step of injecting an amount of spacer fluid into the wellbore further comprises adding an amount of a surfactant to the spacer fluid if the base oil is an incompatible base oil.

10. The method of claim 1, wherein the step of measuring a compositional characteristic of the base oil using one or more analytical tests occurs at a location proximate to the wellbore.

11. The method of claim 1, wherein the step of measuring a compositional characteristic of the base oil using one or more analytical tests occurs at a location apart from the wellbore.

12. A method comprising:
providing a drilling fluid that comprises a base oil;
using the drilling fluid to drill at least a portion of a wellbore penetrating at least a portion of a subterranean formation;
measuring a compositional characteristic of the base oil using one or more analytical tests;
determining whether the base oil is a compatible base oil or an incompatible base oil based at least in part on a comparison of the compositional characteristic of the base oil with one or more known compositional characteristic of a known compatible base oil;
injecting an amount of spacer fluid that comprises an amount of a surfactant into the wellbore, wherein the amount of the surfactant is increased if the base oil is an incompatible base oil; and
injecting one or more cementing or completion fluids into the wellbore.

13. The method of claim 12, wherein the one or more analytical tests comprise a nuclear magnetic resonance spectroscopy test.

14. The method of claim 12, wherein the one or more analytical tests comprise an infrared spectroscopy test.

15. The method of claim 12, wherein the one or more analytical tests comprise a gas chromatography test.

16. The method of claim 12, wherein the one or more analytical tests comprise an ion chromatography test.

17. The method of claim 12, wherein the one or more analytical tests comprise an ultraviolet-visible spectroscopy test.

18. The method of claim 12, wherein the step of injecting an amount of spacer fluid into the wellbore further comprises increasing the amount of the spacer fluid if the base oil is an incompatible base oil.

19. A method comprising:
providing a drilling fluid that comprises a base oil;
using the drilling fluid to drill at least a portion of a wellbore penetrating at least a portion of a subterranean formation;
measuring a compositional characteristic of the base oil using one or more analytical tests;
determining whether the base oil is a compatible base oil or an incompatible base oil based at least in part on a comparison of the compositional characteristic of the base oil with one or more known compositional characteristics of a known compatible base oil;
providing one or more cementing or completion fluids, wherein the one or more cementing or completion fluids comprise a surfactant if the base oil is an incompatible base oil; and
injecting the one or more cementing or completion fluids into the wellbore.

20. The method of claim 19, wherein the one or more analytical tests are selected from the group consisting of: a nuclear magnetic resonance spectroscopy test, an infrared spectroscopy test, a gas chromatography test, an ion chromatography test, an ultraviolet-visible spectroscopy test, and any combination thereof.

* * * * *